(12) United States Patent
Foster

(10) Patent No.: US 8,539,955 B2
(45) Date of Patent: Sep. 24, 2013

(54) MOUTHGUARD

(76) Inventor: Jeff A. Foster, Wausau, WI (US)

( * ) Notice: Subject to any disclaimer, the term of this patent is extended or adjusted under 35 U.S.C. 154(b) by 289 days.

(21) Appl. No.: 13/066,527

(22) Filed: Apr. 15, 2011

(65) Prior Publication Data

US 2012/0260924 A1    Oct. 18, 2012

(51) Int. Cl.
*A61C 5/14* (2006.01)
*A61C 3/00* (2006.01)

(52) U.S. Cl.
USPC ............................................. 128/861; 433/6

(58) Field of Classification Search
USPC ............... 128/846, 857, 859, 861; 433/6, 433/8, 2, 18, 20, 22, 10, 13, 15
See application file for complete search history.

(56) References Cited

U.S. PATENT DOCUMENTS

| 4,527,975 A * | 7/1985 | Ghafari et al. | 433/8 |
| 6,126,443 A * | 10/2000 | Burgio | 433/215 |
| 2009/0220920 A1 * | 9/2009 | Primus et al. | 433/226 |
| 2010/0081106 A1 * | 4/2010 | Park | 433/8 |

\* cited by examiner

*Primary Examiner* — Patricia Bianco
*Assistant Examiner* — Tarla Patel
(74) *Attorney, Agent, or Firm* — Derek L. Prestin

(57) ABSTRACT

An improved mouthguard is provided for use by individuals having orthodontic appliances, such as braces. The mouthguard comprises an outer guard portion and an inner subguard portion. The subguard provides a barrier between the outer guard and the user's braces, thereby allowing the outer guard to be custom fit to the user's mouth and teeth using methods known in the art. Additionally, the subguard is secured to the outer guard, producing a one-piece mouthguard, and allows the mouthguard to be removably secured to the user's braces, increasing the comfort and retention of the mouthguard within the user's mouth. The mouthguard effectively protects the users braces, as well as the user's teeth and mouth, from potential damage arising out impacts suffered by the user during sporting activities while improving the user's comfort and performance in sports by allowing the user to breathe and speak uninhibited during the sporting activity.

13 Claims, 18 Drawing Sheets

MOUTHGUARD

BACKGROUND OF THE INVENTION

The invention disclosed herein relates an oral appliance and, more specifically, a mouthguard for use in sporting applications. The present invention provides a mouthguard which may be used by an individual having orthodontic appliances, such as braces, when the individual is participating in sporting activities and other similar activities.

Mouthguards have been developed and sold for several years for use in connection with sporting activities, such as contact sports like football and hockey, and other similar activities. Mouthguards are commonly used as part of these sporting activities to protect the mouth and teeth of a participant from damage that may result from impacts suffered by the participant as part of the sporting activity. Such mouthguards range from inexpensive devices which are premoulded and non-adjustable to more expensive orthodontic devices that are fitted by dentists or orthodontists.

Mouthguards generally consist of a U-shaped device that cushions the impact of the upper and lower teeth of the user and protects the user's teeth in response to a jarring action or impact.

Mouthguards are typically made from plastics material such as an ethylene vinyl acetate copolymer (EVA) and fall into two general categories. The mouthguards are often either stock products premoulded and made in a variety of sizes, or are a product that may be moulded to suit the physical characteristics of the user. The stock mouthguards are typically the cheapest and least effective in use, while the custom moulded and shaped mouthguards are the most expensive and effective in their impact absorbent properties.

Several prior art mouldable mouthguards are made from ethylene vinyl acetate (EVA), which is a softenable thermoplastic. The softening point of EVA is less than the temperature of boiling water. Therefore, a mouthguard made from EVA may be formed, or custom fit, to the user's mouth by placing the mouthguard in hot water until it becomes soft, placing it in the user's mouth, and having the user bite down into the mouthguard. Such a mouthguard, after cooling, then retains the shape of the user's teeth and mouth.

A more expensive type of mouthguard is a custom mouthguard generally provided by dentists. The "custom-fitted" dentist-provided mouthguards are manufactured directly from an impression taken of the user's teeth and jaw. A plastic material is then formed around a mould generated from the impression, resulting in a mouthguard that is custom-fitted to the user's mouth and teeth.

A traditional mouthguard for individuals with braces is simply placed in the user's mouth. Currently marketed non-mouldable mouthguards for braces or other dental appliances are composed of medical grade silicone, or other high temperature materials that cannot be heated or boiled for fitting around the teeth and gums. Because such traditional mouthguards cannot be fitted to the individual user, they tend to move around in the user's mouth, making it difficult to breathe and speak, and they fail to provide adequate protection, depending at least in part upon the position at the time of impact. Additionally, since the traditional mouthguards tend to move around in the user's mouth, they often are not very comfortable for the user and, as a result, a user will often forgo using the mouthguard to remain more comfortable, leading to an increased incidence of injuries to the user's mouth and/or teeth due to impacts suffered by the user during the user's participation in the sporting activity.

However, if EVA or a similar low temperature melting plastic is used as part of a mouldable mouthguard in conjunction with braces or other orthodontic appliances, the softer thermoplastic easily becomes entangled with the braces and may cause damage to the braces or inconvenience to the user, such as shifting, broken wires, or debanded brackets.

Because every mouth has a different shape, a non-fitted mouthguard is inadequate for a great number of wearers. In addition, impact absorption increases with improved fit, meaning that fitted mouthguards have superior injury prevention characteristics. Therefore, there is a need for an improved mouthguard which may be fitted or formed for users having braces.

BRIEF SUMMARY OF THE INVENTION

It is a feature of the present invention to provide a mouthguard for use by individuals having orthodontic appliances, such as braces, when such individuals are participating in sporting activities, such as contact sports like football, hockey, or other sports, and other similar activities.

The present invention aims to provide a mouthguard which in one aspect has the effect of providing a mouthguard which may be simply and easily used by a participant in sporting activities. The present invention also aims to provide a mouthguard which is relatively inexpensive and which may be manufactured in a small number of general sizes designed to fit the majority of users that may then be directly moulded by the end user to be custom-fit to the user's mouth and teeth.

The general objective of the invention is to provide an improved mouthguard. Another objective is to provide an improved mouthguard that is capable of being custom-fitted to the teeth of an individual having braces or other dental or orthodontic appliances. Still another objective is to provide a mouldable or fitted mouthguard that provides protection to those with braces, while still remaining comfortable to wear. It is a further objective of the invention to provide a mouthguard comprising two portions: (1) an outer guard portion that comes into contact with the bottom of a wearer's teeth that is softenable and formable, and (2) a subguard portion which comes in contact with the outer surface of a user's teeth or the user's braces, that is not softenable and formable and also includes a means for removably engaging the user's braces.

The present invention also aims to provide a mouthguard that may be used in sporting activities that is comfortable for a user to wear, which effectively protects any orthodontic appliances, such as braces, that the user has, and which protects the user's teeth and mouth and/or the user's orthodontic appliances from potential damage arising out of impacts suffered by the user during the sporting activity, thereby improving the participant's comfort and performance in sports. The present invention also aims to provide a mouthguard that exhibits improved retention within the user's mouth, which allows the user to breathe and speak uninhibited during the sporting activity.

Traditionally, orthodontic patients have had limited choices to protect their orthodontic appliances and mouth while participating in sporting activities. The present invention addresses several of these prior limitations and offers a practical and safe solution to such patients. Traditional mouthguards do not fit well when the patient is wearing orthodontic appliances and often fall out or remain loose in the patient's mouth. The mouthguard of the present invention offers superior retention, leading to decreased wear on the mouthguard, easier breathing by the patient, and reduced risk of injury. The design of the present invention, namely the use of an outer guard to protect the teeth and mouth of the patient and the subguard to secure the mouthguard to the patient's orthodontic appliances, allows patients to breathe and communicate better during sporting activities, while giving the patient confidence that the mouthguard will protect their mouth and teeth. In particular, athletes participating in team sports will be able to communicate more effectively without having to remove their mouthguard.

Since the mouthguard of the present invention is more comfortable and better retained within the patient's mouth, more patients will be inclined to wear a mouthguard during sporting activities, thereby protecting the patient's mouth, teeth, and orthodontic appliances. This increased use of mouthguards could save patients significant amounts in dental bills and aid in the reduction in broken components of orthodontic appliances. From the perspective of dentists and orthodontists, the greater use of mouthguards would reduce the odds that a patient will come to an appointment with broken components of their orthodontic appliances. Overall, this increased mouthguard use will reduce a patient's time in their orthodontic appliances and will reduce the patient's dental costs.

DETAILED DESCRIPTION OF THE PREFERRED EMBODIMENT(S)

Figure 1:
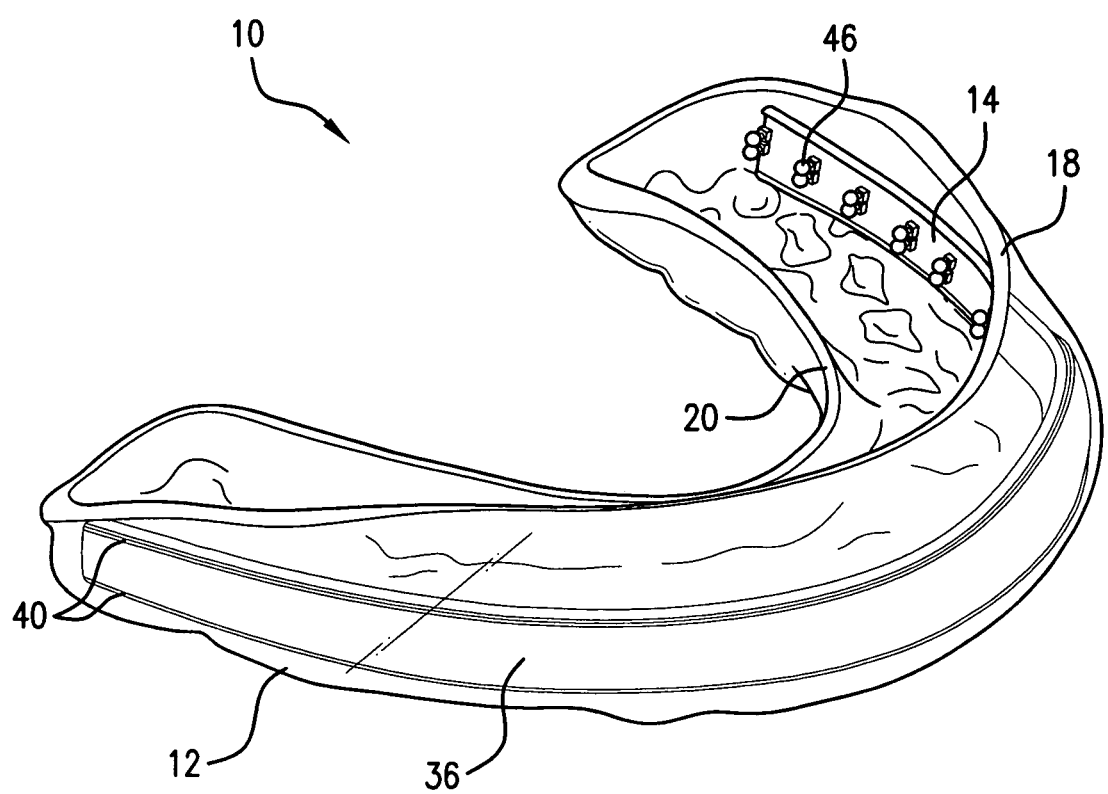
FIG. 1 is a perspective view of the mouthguard of the present invention.
Figure 2:
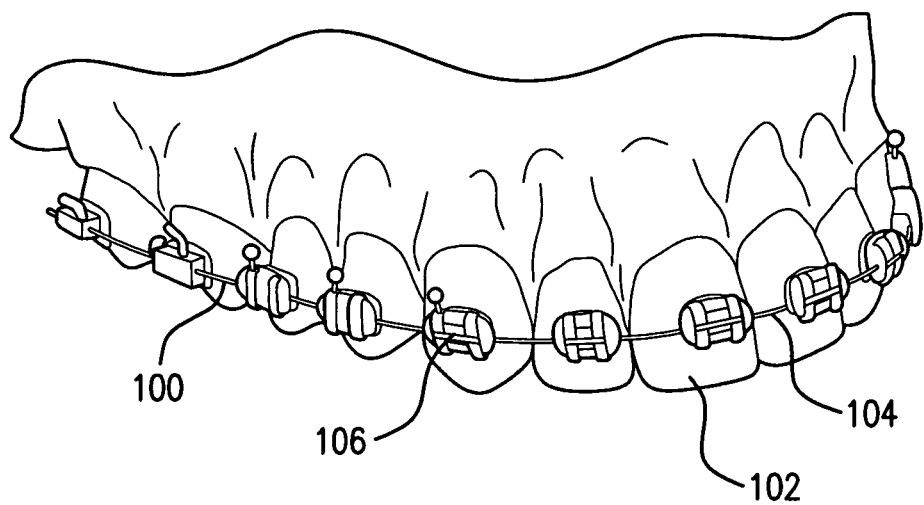
FIG. 2 is a perspective view of a user's top jaw with braces.

As shown in FIGS. 1 and 18-22, there is illustrated a first form of a mouthguard 10 according to the present invention. A preferred embodiment of the present invention provides an improved mouthguard 10 for use by individuals having orthodontic appliances, such as braces 100 as shown in FIG. 2. The mouthguard 10 of the present invention comprises an outer guard portion 12 and an inner subguard portion 14.

The outer guard portion 12 of the mouthguard 10 includes base portion 16 having a somewhat parabolic or U-shaped (or C-shaped) plan form, so as to be locatable between the teeth of the upper and lower jaws of a user and to substantially follow the teeth pattern and jaw shape of the user.

The base portion 16 of the outer guard 12 includes an outer or mesial flange 18 portion and an inner or distal flange 20 portion that extend generally upwardly from the base portion 16 along the outer mesial edge 22 and inner distal edge 24 of the base portion 16, respectively. The outer flange 18 and inner flange 20 extend to one side of the base portion 16. Preferably, the outer flange 18 and inner flange 20 extend from the base portion 16 upwards toward the roof of the user's mouth when the mouthguard 10 is placed within the user's mouth. As such, the outer flange 18 and inner flange 20 define, along with the base portion 16, a channel 26 for accepting the teeth 102 of the upper jaw. The outer flange 18 and inner flange 20 are shaped to the mesial and distal aspects of the upper jaw of the user.

The base portion 16 of the outer guard 12 has a cross sectional form adapted to substantially occupy the space between the teeth of the user's upper and lower jaws when the user closes his or her mouth, so as to provide a support for the jaws of the user, while still being thin enough to remain comfortable to the user. Preferably, the base portion 16 is of somewhat consistent thickness. However, alternatively the base portion 16 may vary thickness between the leading or mesial end 28 of the mouthguard 10 and the trailing or distal ends 30 of the mouthguard 10 in such a way as to better fit the user's mouth structure and configuration of teeth.

Figure 3:
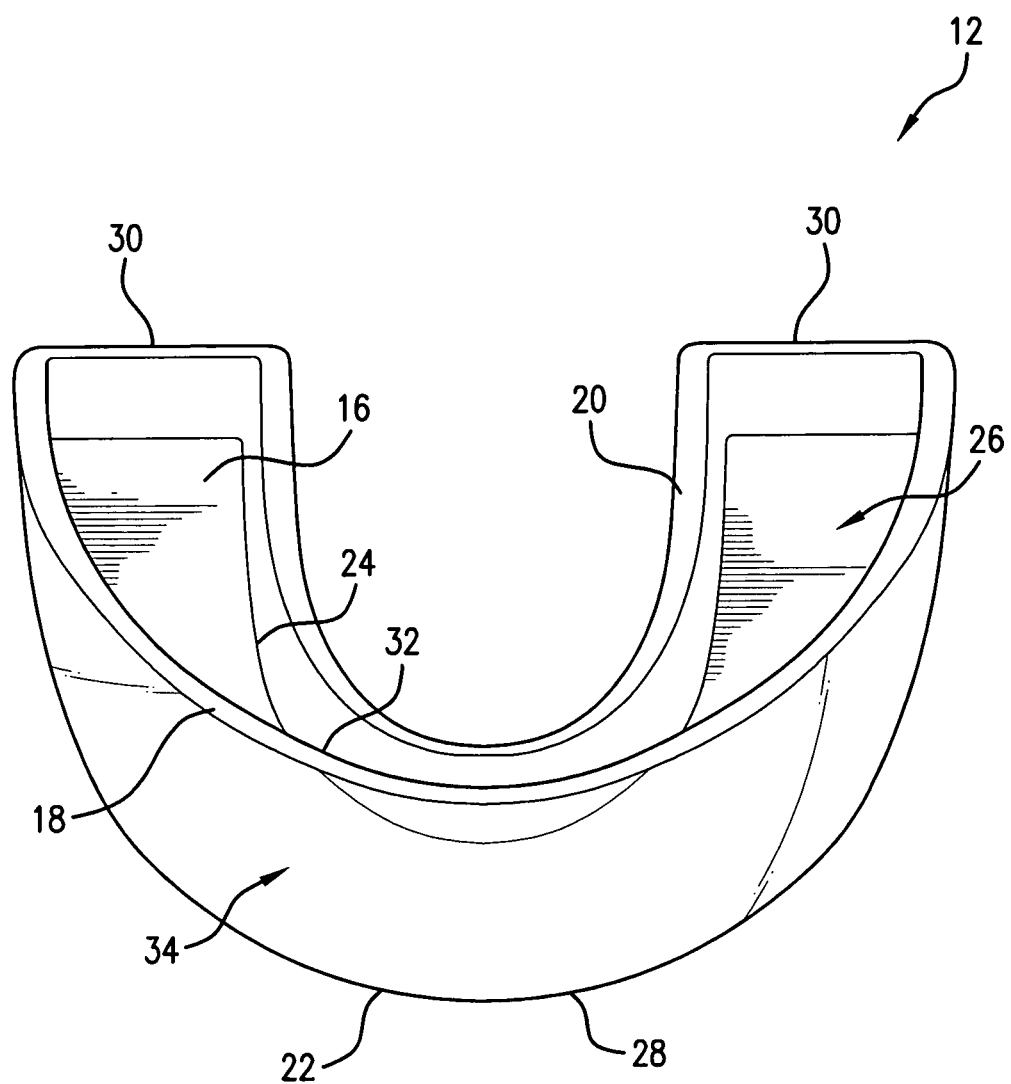
FIG. 3 is a perspective view of the outer guard of the mouthguard of FIG. 1 viewed from the top of the outer guard and before the outer guard has been fitted to the user.
Figure 4:
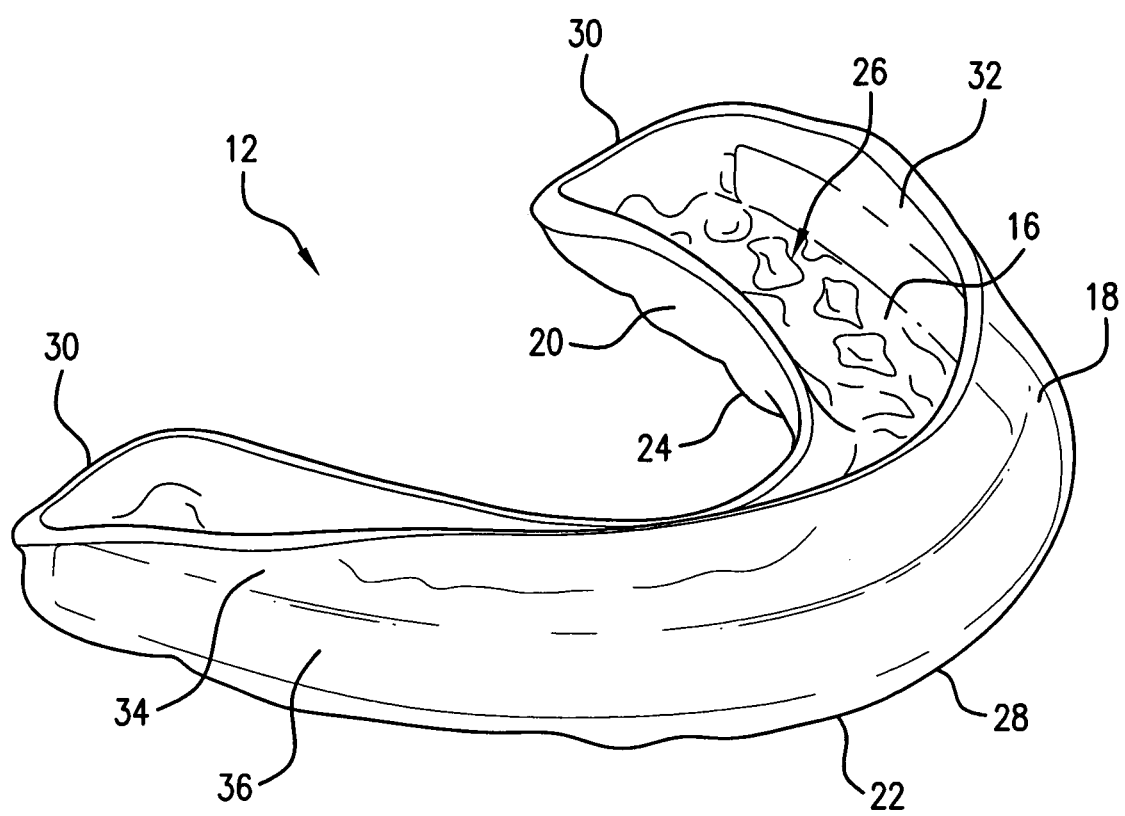
FIG. 4 is a perspective view of the outer guard of the mouthguard of FIG. 1 viewed from the top of the outer guard and after the outer guard has been fitted to the user.
Figure 5:
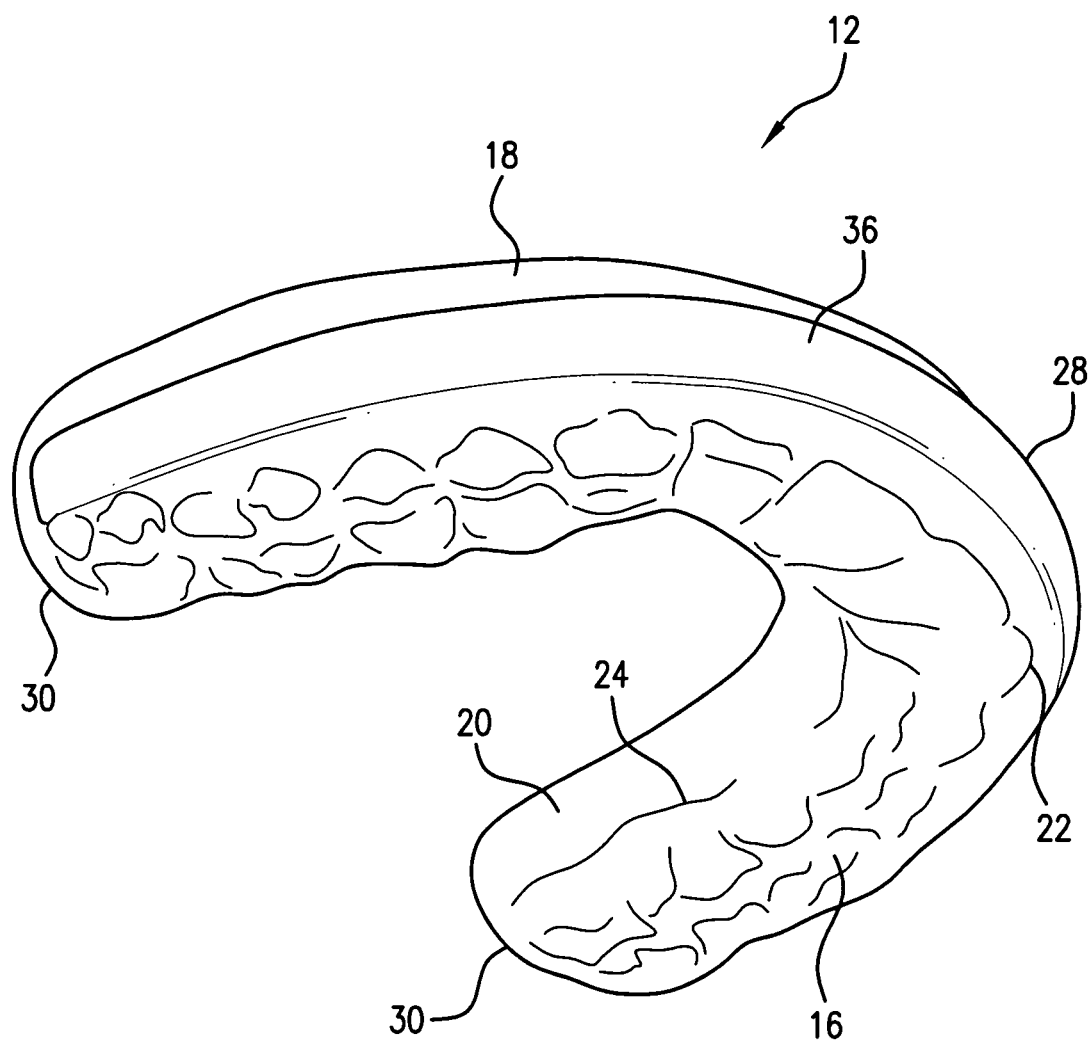
FIG. 5 is a perspective view of the outer guard of the mouthguard of FIG. 1 viewed from the bottom of the outer guard and after the outer guard has been fitted to the user.
Figure 6:
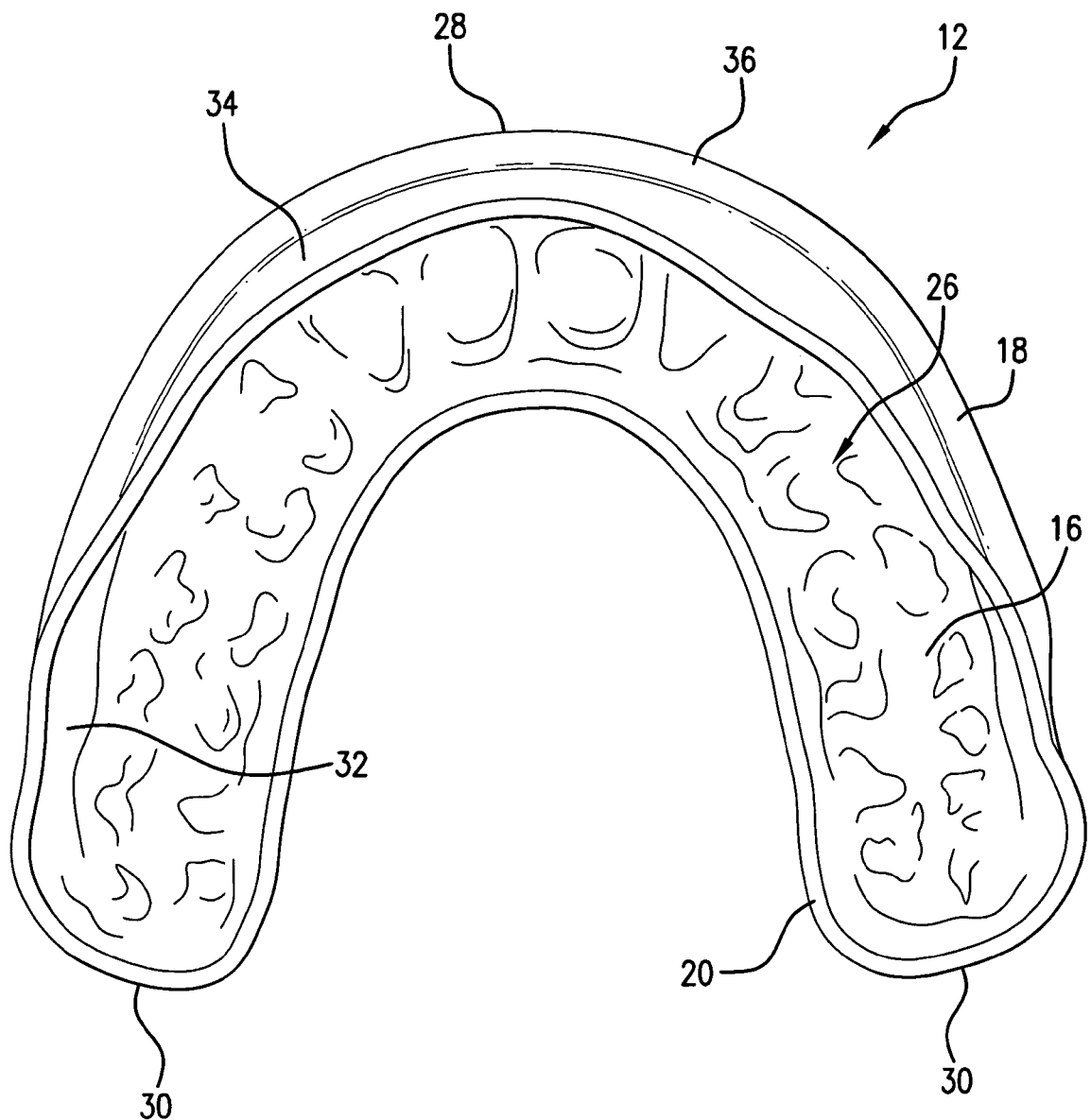
FIG. 6 is a plan view of the outer guard of the mouthguard of FIG. 1 viewed from the top of the outer guard and after the outer guard has been fitted to the user.

As shown more clearly in FIGS. 3-4 and 6, the outer flange 18 and inner flange 20 define the channel 26 for receipt of the teeth 102 of the upper jaw, with the channel 26 preferably increasing in width from the mesial end of the mouthguard 10 to the distal ends thereof in order to best conform to the normal configuration and width of an individual's teeth. That is, the channel 26 has a smaller width at the mesial end 28 of the mouthguard 10 since incisors are generally thinner in size and the channel 26 has a greater width at the distal ends 30 of the mouthguard 10 since molars are generally thicker in size. The outer flange 18 and inner flange 20 also taper in height from the mesial end of the mouthguard 10 to the distal ends thereof.

Figure 7:
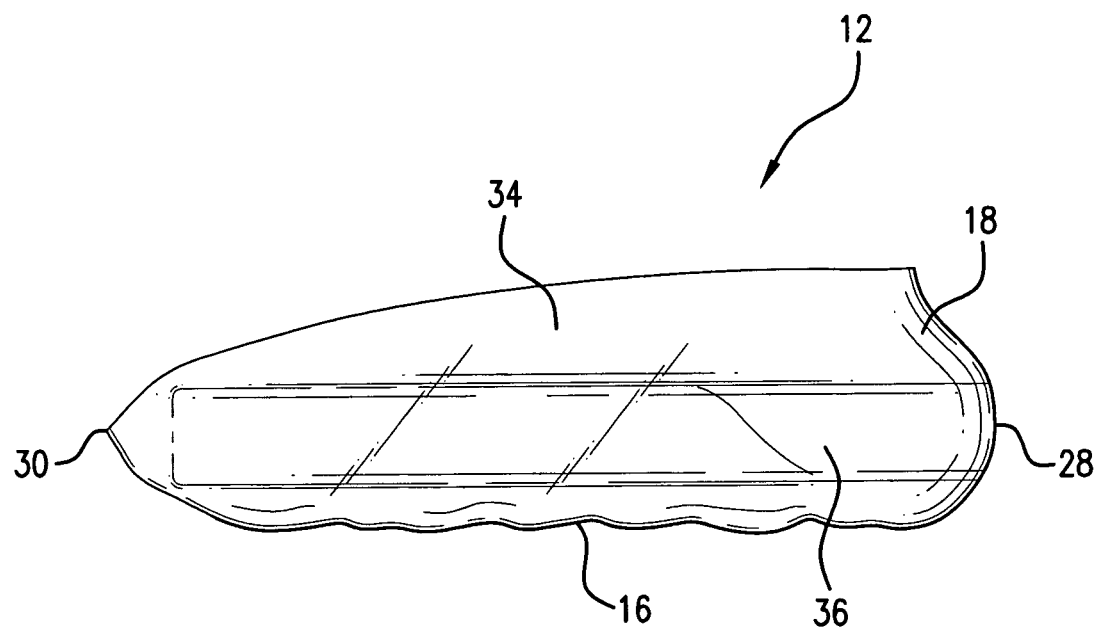
FIG. 7 is a side elevation view of the outer guard of the mouthguard of FIG. 1 viewed from the top of the outer guard and after the outer guard has been fitted to the user.

As is more apparent in FIG. 7, the outer flange 18 is inclined to the vertical away from the leading end of the mouthguard 10 on opposite sides of the base portion 16. The angle of inclination of the outer flange 18 on the upper side of the base portion 16 decreases from a maximum at a position at the leading mesial end 28 of the mouthguard 10 to zero (i.e.

substantially perpendicular to the base portion X16) toward the trailing distal ends 30 of the mouthguard 10. As such, the outer flange 18 is sloped inward toward the user's teeth and gums to conform to the natural slope of the user's teeth and gums.

The outer flange 18 of the mouthguard 10 has an inner surface 32 which faces the user's braces 100 and an outer surface 34 which would come in contact with the inside of the user's mouth when the user's mouth is closed, or be exposed when the user's mouth is open.

The outer flange 18, and more specifically the inner surface 32 of the outer flange 18, also defines a subguard channel 36 that is adapted to receive the subguard 14 when the outer guard 12 is fitted to the user's teeth 102. The subguard channel 36 naturally forms when the outer guard 12 is fitted to the user's teeth 102 because the subguard 14 covers the orthodontic appliances, such as braces 100, of the user and therefore the subguard 14 projects from the surface of the user's teeth 102. The subguard channel 36 is therefore sized according to the size and configuration of the subguard 14.

Where, as later described herein, the subguard 14 is mechanically engaged by the outer guard 12, the subguard 14 may directly occupy the subguard channel 36 of the outer guard 12, such that the subguard channel 36 is substantially occupied by the subguard 14 immediately upon its formation. Alternatively, where an adhesive is used to secure the subguard 14 to the outer guard 12, as later described herein, the subguard channel 36 may not be occupied by the subguard 14 until the subguard 14 is adhered to the outer guard 12 with an adhesive.

The inner flange 20 also defines a concave recess for receiving the tongue of the user. The inner flange 20 is of a generally parabolic plan form, so as to define a rearwardly-directed recess for encompassing the tongue of the user in its correct anatomical position in the mouth. As such, the configuration of the inner flange 20 improves the comfort and retention of the mouthguard 10 in the oral cavity.

The inner flange 20 comes in contact with distal side of the user's teeth 102.

The outer guard 12 of the mouthguard 10 may be constructed of any shock-absorbent material that is known in the art that may be used in the mouth of a person, such as medical-grade silicon, an ethylene vinyl acetate copolymer (EVA), poly vinyl acetate-ethylene, ethyl vinyl acetate, thermal plastic, or a dental resin such as Essix®. In the preferred embodiment, the outer guard 12 of the mouthguard 10 is made from EVA or a similar low temperature melting plastic having a melting point lower than the boiling point of water, such that the outer guard 12 may be boiled and fitted by the user, thereby making the outer guard 12 formable or moldable in hot water. This allows the outer guard 12 to mould to the general shape of the user's teeth and mouth, thereby being fitted to the user's mouth and teeth.

Most preferably, the outer guard 12 is made of a material that allows the outer guard 12 to be fitted to the user's mouth and teeth using the "boil and bite" process known in the prior art. The "boil and bite" process involves boiling the outer guard 12 in water for a time sufficient to soften the outer guard 12. The outer guard 12 is then placed in the user's mouth, after the subguard 14 has been secured to the user's orthodontic appliances 100 as discussed herein, and the user firmly bites down on the outer guard 12. In conjunction with biting, the user will also need to apply sufficient lip pressure, generally by pressing on their lips with their fingers, to conform the mesial flange 22 of the outer guard 12 to the shape of the user's teeth and jaw and to embed the subguard 14, and specifically the ridges 40 of the subguard 14, into the outer guard 12. Since the outer guard 12 has been softened by boiling the outer guard 12 in water, the outer guard 12, in response to the pressure from the user's mouth, teeth, and jaws, will conform to the shape and configuration of the user's mouth and teeth. Once the outer guard 12 begins to cool and becomes less soft and pliable, the outer guard 12 is then removed from the user's mouth and is allowed to fully cool, which causes the outer guard 12 to harden and set. Once the outer guard 12 has fully cooled, it retains its shape and is therefore fitted to the user's mouth and teeth. FIG. 3 depicts the outer guard 12 prior to it being fitted to the teeth 102 of the user using the "boil and bite" method discussed herein, while FIGS. 4-7 show the outer guard 12 after it has been fitted to the teeth 102 of the user.

Preferably, the outer guard 12 of the mouthguard 10 is of substantially uniform thickness throughout the outer guard 12. More preferably, the outer guard 12 of the mouthguard 10 has a thickness of at least three (3) millimeters but less than four (4) millimeters, as it has been found that thicknesses of greater than four (4) millimeters do not proportionally increase the protection provided by the outer guard 12 while such larger thicknesses reduce the comfort of the mouthguard 10 due to the greater size of the outer guard 12. Alternatively, the thickness of the outer guard 12 of the mouthguard 10 may be any thickness that is sufficient to provide suitable protection to the user's teeth and orthodontic appliances 100, while still remaining comfortable in the user's oral cavity.

Optionally, where the mouthguard 10 is intended to be used in connection with a sporting activity where helmets are utilized, the mouthguard 10 may also include a retainer strap or another connector for connection of the mouthguard 10 to a football helmet or hockey helmet, or similar equipment, as in the prior art.

The subguard 14 of the mouthguard 10 preferably has a somewhat parabolic or U-shaped (or C-shaped) configuration when viewed from the top of the subguard 14, provided, however, that the subguard 14 is preferably made of a flexible material, such that the subguard may be produced, packaged, shipped, and/or purchased in a substantially flat form and then curved to the parabolic or U-shaped form by the user when the subguard 14 is attached to the user's orthodontic appliances, such as braces 100, and teeth 102.

The subguard 14 of the mouthguard 10 preferably has a roughly rectangular shape when viewed from the mesial or distal sides of the subguard 14, with the subguard 14 being substantially longer in the horizontal plane than in the vertical plane.

Figure 8:
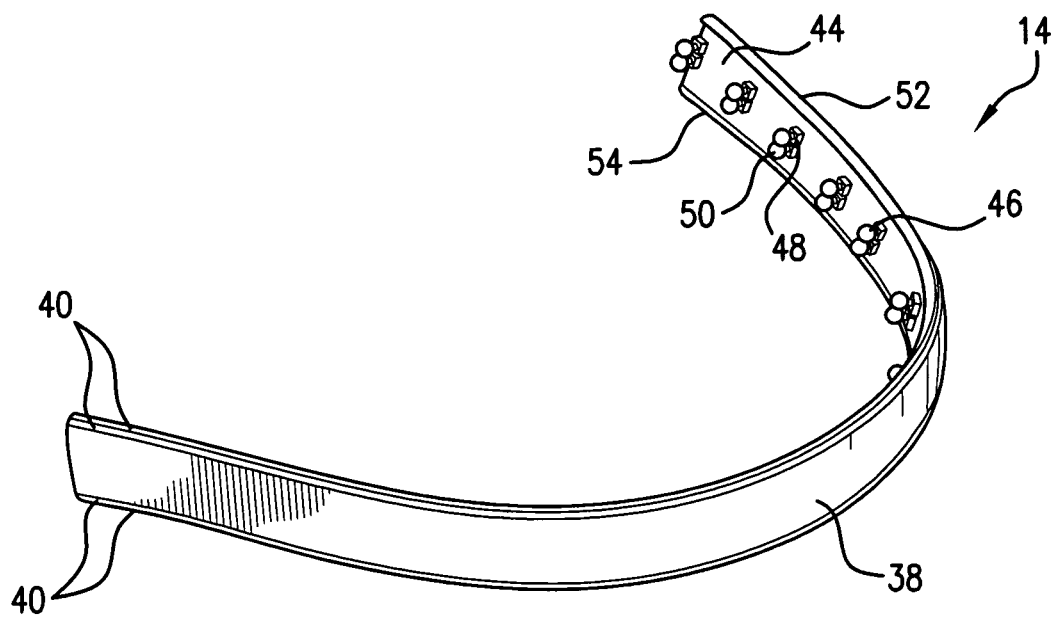
FIG. 8 is a perspective view of the subguard of the mouthguard of FIG. 1 viewed from the front of the subguard.
Figure 9:
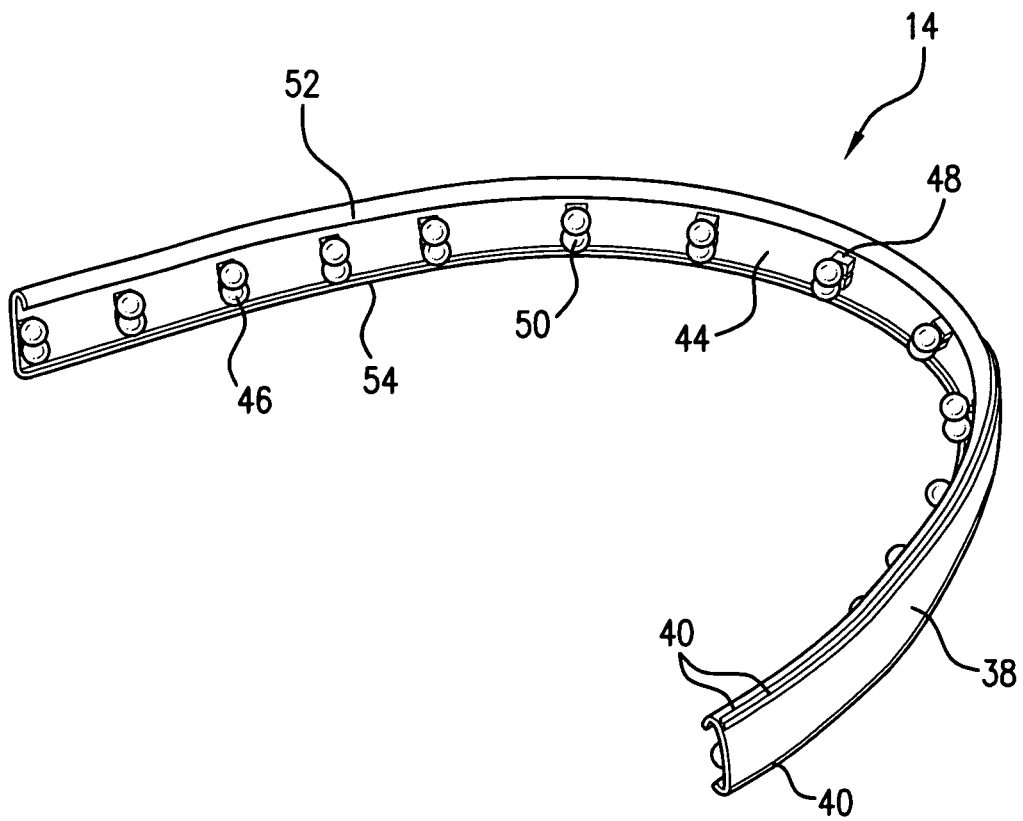
FIG. 9 is a perspective view of the subguard of the mouthguard of FIG. 1 viewed from the rear of the subguard.
Figure 10:
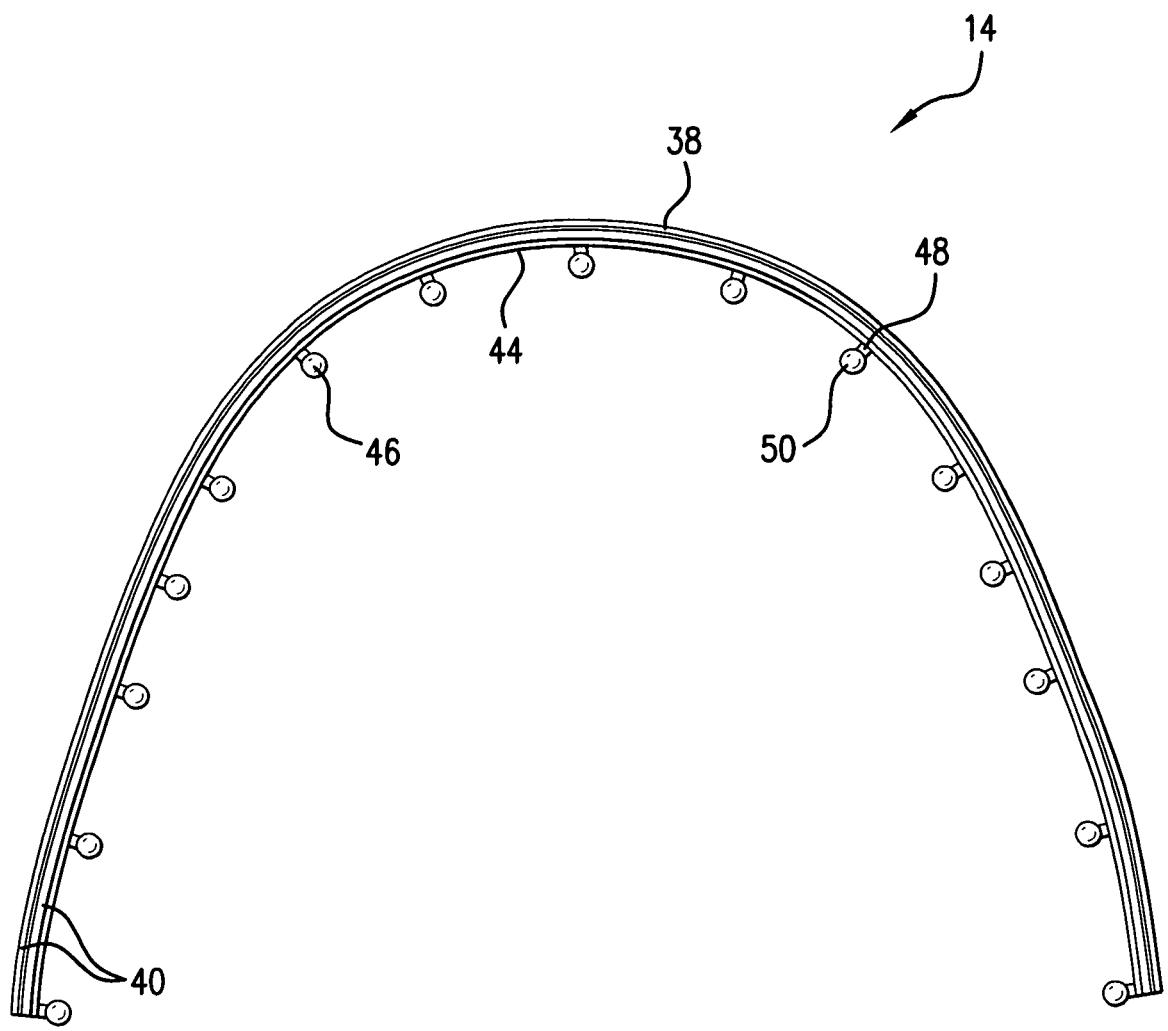
FIG. 10 is a plan view of the subguard of the mouthguard of FIG. 1 viewed from the top of the subguard.

As shown in FIGS. 8-10, the horizontal length of the subguard 14 is preferably sized such that the subguard 14 has a length that is substantially the same as, or more preferably slightly greater than, the length of the user's orthodontic appliances 100. As a result, the mesial side of the user's orthodontic appliances, such as braces 100, are substantially covered by the subguard 14. Likewise, the vertical width of the subguard 14 is preferably sized such that the subguard 14 has a width that is substantially the same as, or more preferably slightly greater than, the width of the largest part of the user's orthodontic appliances 100. For example, where the user's orthodontic appliances are standard orthodontic braces 100, the length of the subguard 14 would be equal to or greater than the length of the orthodontic arch wire 104 of the braces 100 and the width of the subguard 14 would be equal to or greater than the width of the brackets 106 of the braces 100.

Figure 14:
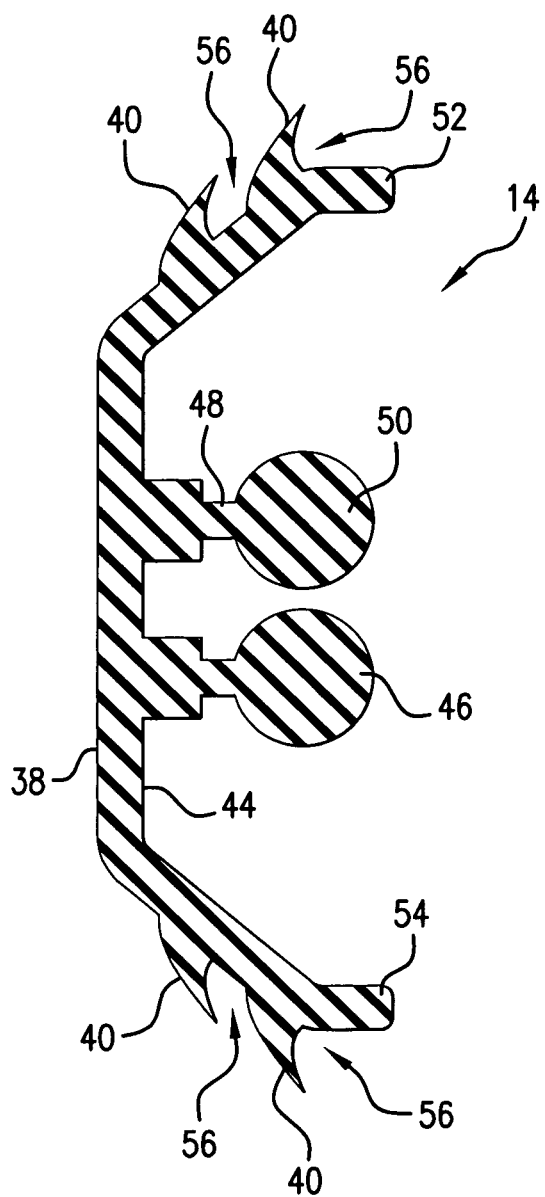
FIG. 14 is a cross-sectional view of the subguard of the mouthguard of FIG. 1.
Figure 16:
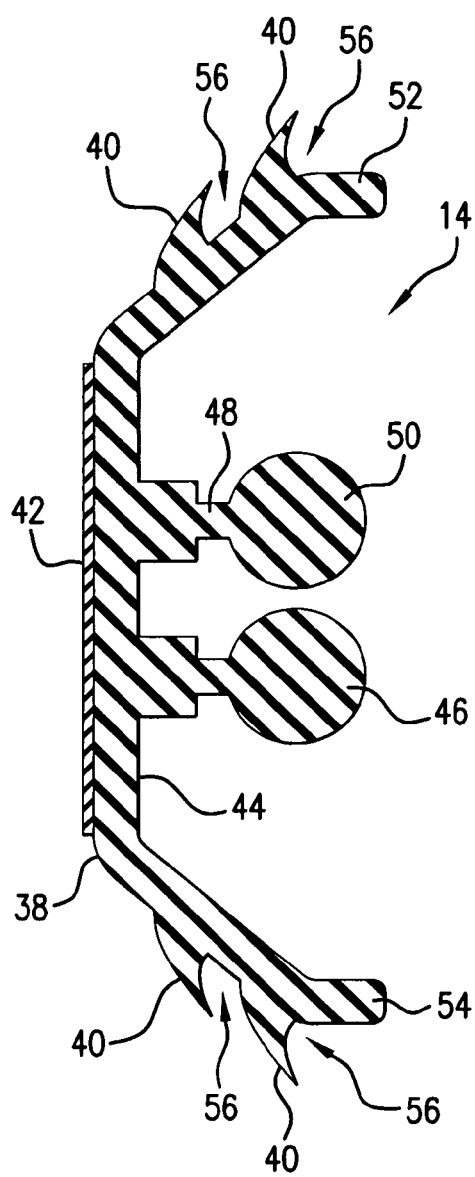
FIG. 16 is a cross-sectional view of a second alternative configuration of the subguard of the present invention.
Figure 17:
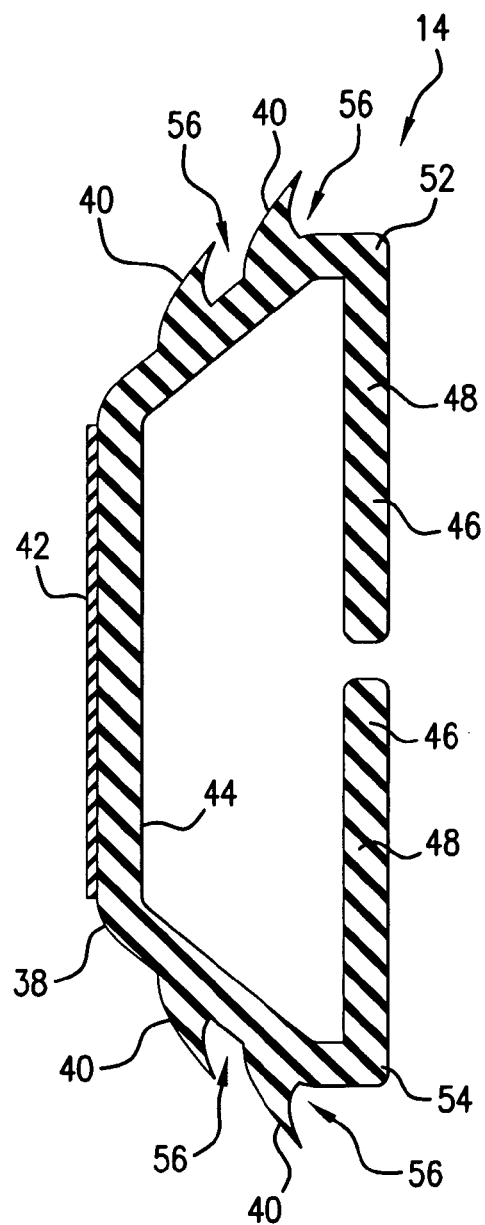
FIG. 17 is a cross-sectional view of a third alternative configuration of the subguard of the present invention.
Figure 18:
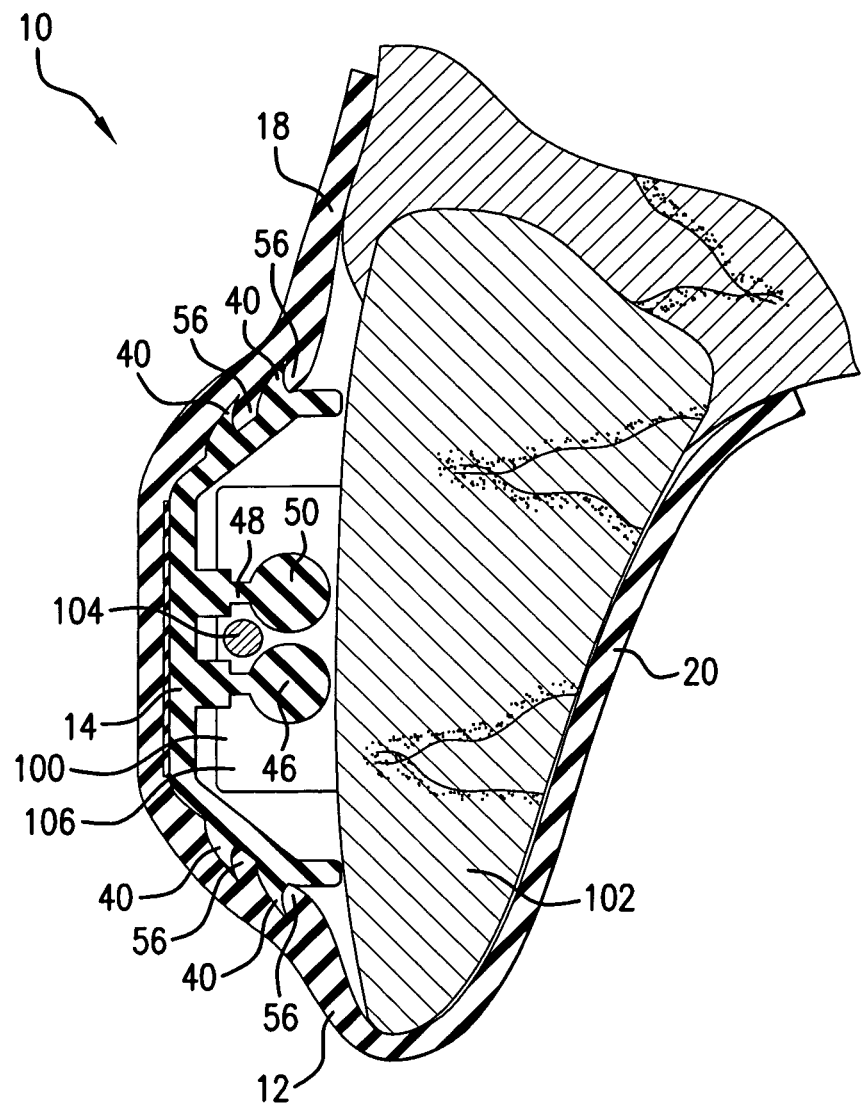
FIG. 18 is a cross-sectional view of the mouthguard of FIG. 1 shown secured to the braces of a user.
Figure 19:
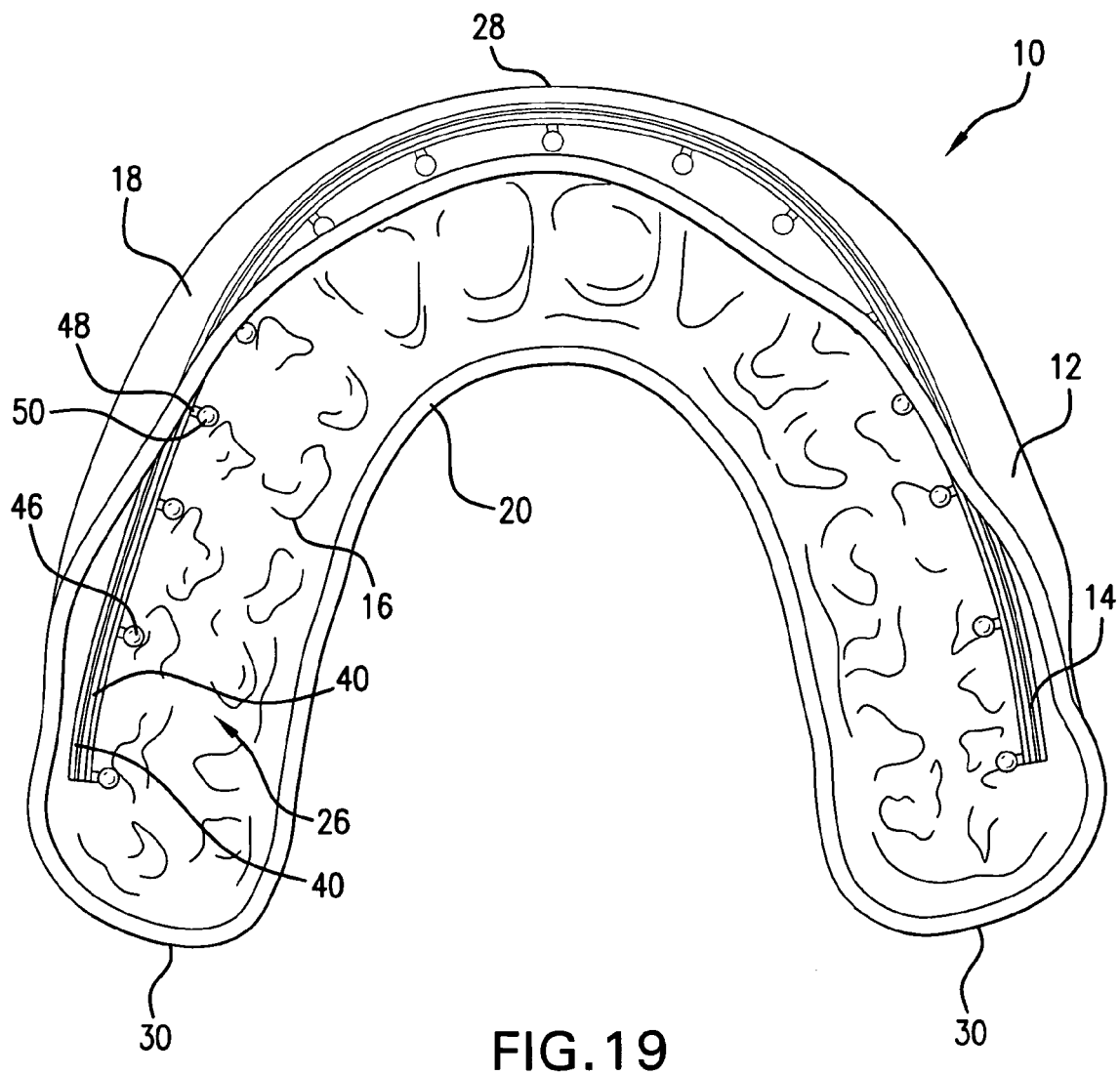
FIG. 19 is a plan view of the mouthguard of FIG. 1 viewed from the top of the mouthguard.
Figure 20:
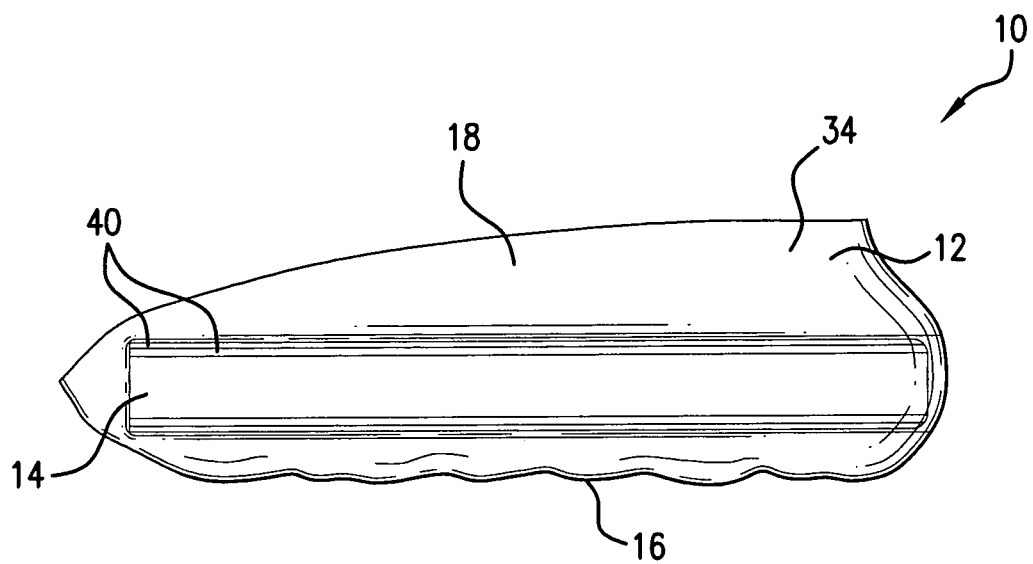
FIG. 20 is a side elevation view of mouthguard of FIG. 1.
Figure 21:
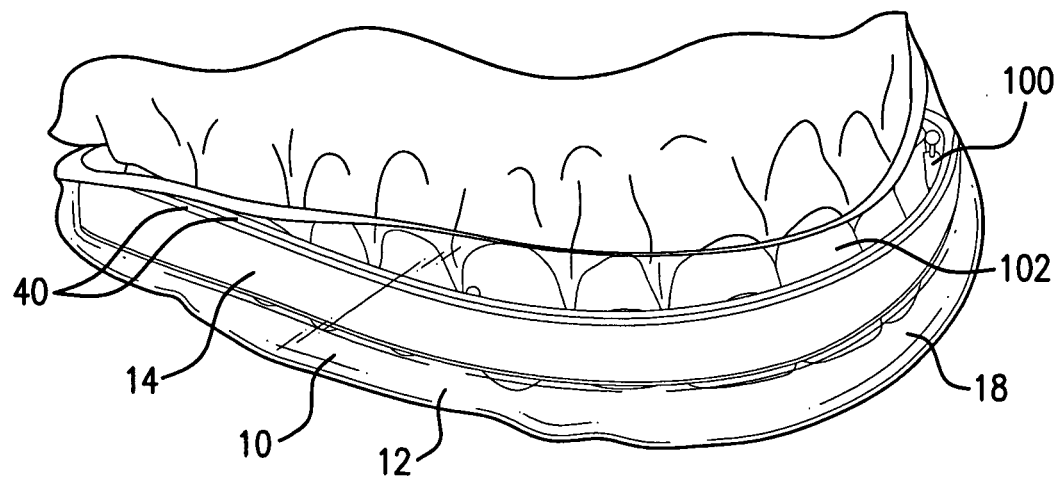
FIG. 21 is a perspective view of the mouthguard of FIG. 1 secured to the braces of a user.
Figure 22:
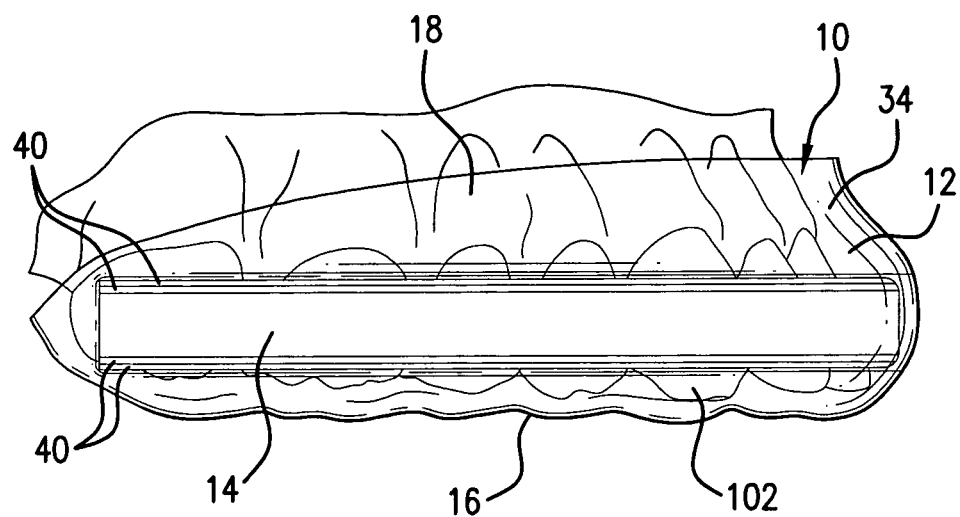
FIG. 22 is a side elevation view of the mouthguard of FIG. 1 secured to the braces of a user.

The mesial side 38 of the subguard 14 includes the means for securing the subguard 14 to the outer guard 12. The means for securing the subguard 14 to the outer guard 12 may take a variety of forms. Preferably, the subguard 14 is secured to the outer guard 12 using ridges 40 or adhesives, such as an adhesive strip 42, as later described herein. As shown in FIGS. 14 and 18, where the subguard 14 is secured to the outer guard 12 using ridges 40, the mesial side 38 of the subguard 14 includes the ridges 40. As shown in FIGS. 14 and 16-17, where an adhesive strip 42 will be utilized to secure the subguard 14 to the outer guard 12, the mesial side 38 of the subguard 14 may include the adhesive strip 42.

Alternatively, where the mesial side 38 of the subguard 14 does not include a separate means for securing the subguard 14 to the outer guard 12, such as where a separate adhesive applied by the user will be used to secure the subguard 14 to the outer guard 12, the surface of the mesial side 38 of the subguard 14 may be substantially flat and smooth.

The distal side 44 of the subguard 14 includes the means for securing the subguard 14 to the user's orthodontic appliances 100. The means for securing the subguard 14 to the orthodontic appliances of the user, such as braces 100, may take a variety of forms. Preferably, the subguard 14 includes a plurality of extensions 46 that project from the surface of the distal side 44 of the subguard 14. More preferably, the extensions 46 are located in pairs that project from the distal side 44 of the subguard 14.

Figure 12:
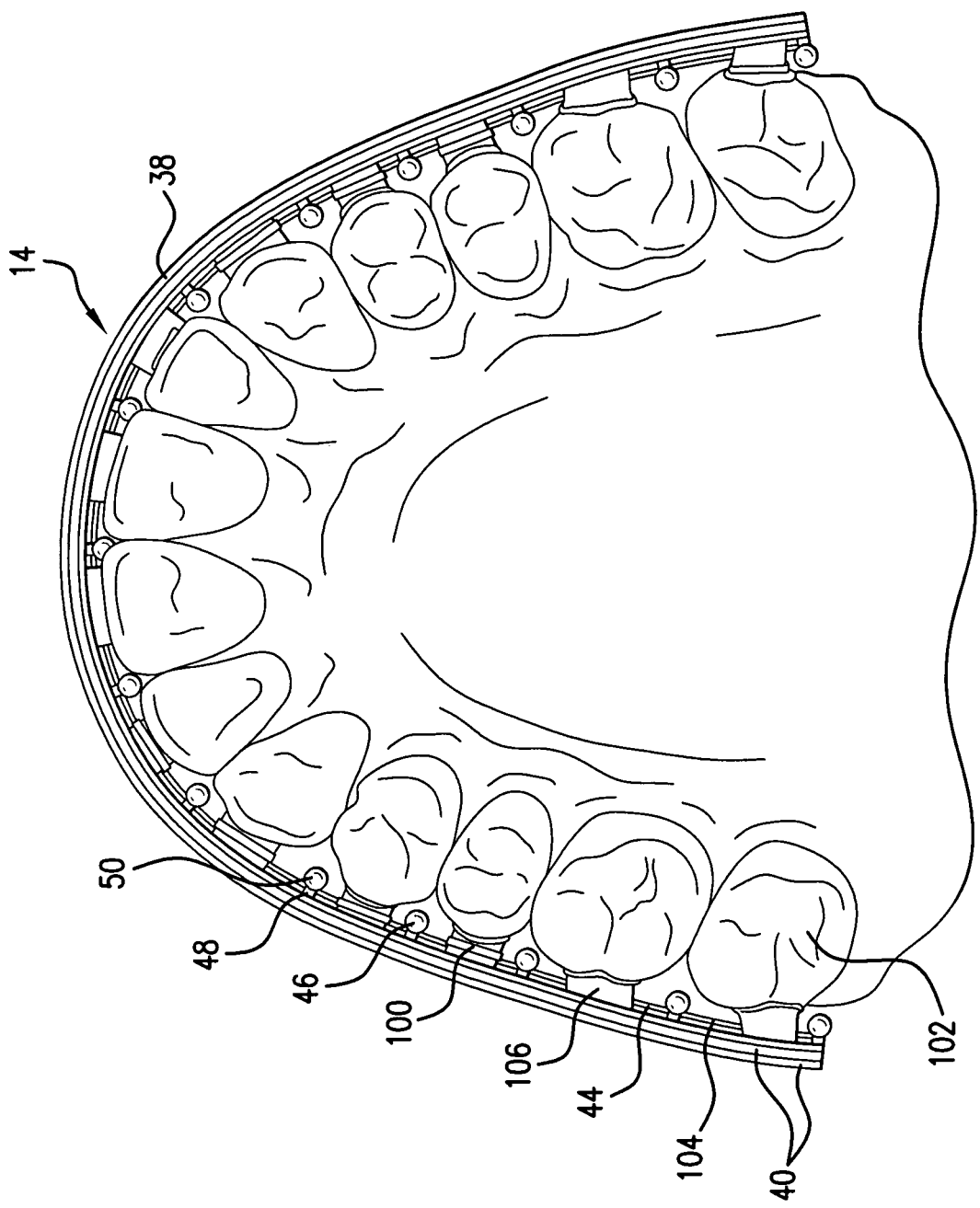
FIG. 12 is a plan view of the subguard of the mouthguard of FIG. 1 viewed from the top of the subguard, with the subguard shown secured to the braces of a user.

As best seen in FIG. 12, the extensions 46 of the subguard 14 are positioned in a separated or staggered configuration and are located such that they are in the best positions for engaging the user's orthodontic appliances 100. For example, where the orthodontic appliances are braces 100, the extensions 46 of the subguard 14 are positioned such that the positions of the extensions 46 correspond with the gaps between the brackets 106 on the user's teeth, such that the extensions 46 line up with locations on the braces 100 where there is only the orthodontic arch wire 104, thereby avoiding the brackets 106.

In the preferred embodiment, as best seen in FIG. 14, pairs of extensions 46 extend from the surface of the distal side 44 of the subguard 14 in roughly the middle of the distal side 44 of the subguard 14, and each extension 46 includes a flexible extension arm 48 and a spherical or ball-shaped tip 50. The spherical tip 50 is attached to the subguard 14 by the extension arm 48. The purpose of the spherical tip 50 is to allow the subguard 14 to be firmly, but easily and removably, attached to the orthodontic arch wire 104 of the user.

Figure 11:
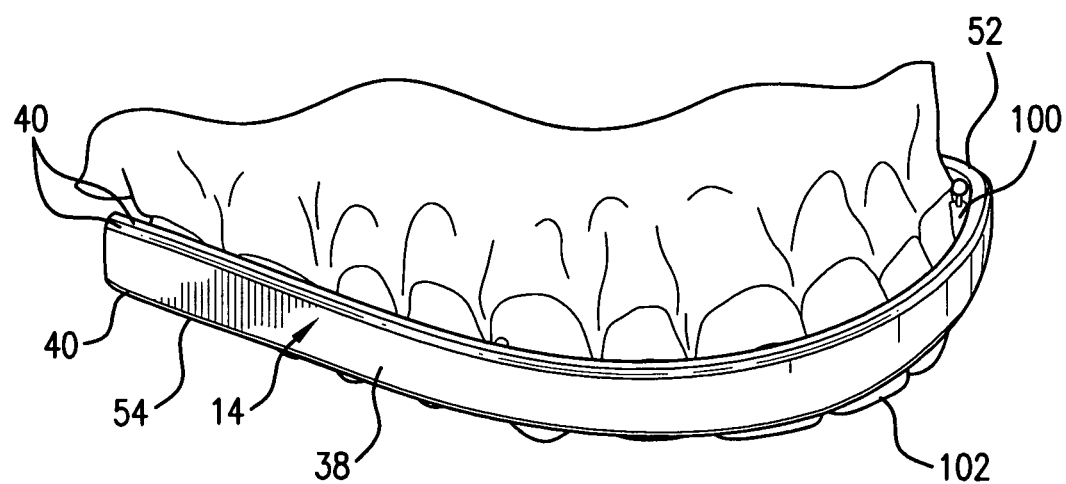
FIG. 11 is a perspective view of the subguard of the mouthguard of FIG. 1 viewed from the front of the subguard, with the subguard shown secured to the braces of a user.
Figure 13:
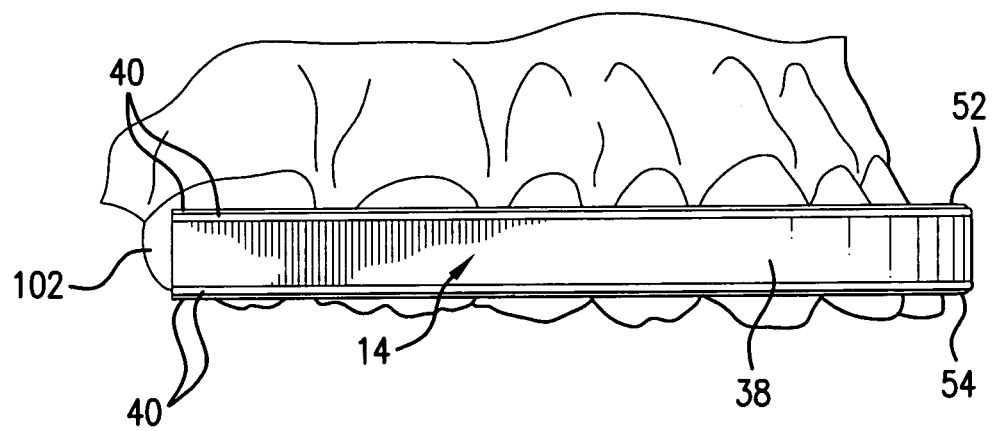
FIG. 13 is a side elevation view of the subguard of the mouthguard of FIG. 1, with the subguard shown secured to the braces of a user.

For example, where the orthodontic appliances of the user are braces 100, the spherical tip 50 allows the subguard 14 to be attached to the orthodontic arch wire 104 of the braces 100. The extension arms 48 allow the spherical tips 50 to be separated for insertion around the orthodontic arch wire 104. That is, as the subguard 14, and the mouthguard 10, is pressed against the user's braces 100 and teeth 102, the shape of the spherical tip 50 and the flexibility of the extension arm 48 allows the spherical tip 50 to deflect around the orthodontic arch wire 104. Once the spherical tip 50 clears the orthodontic arch wire 104 the extensions 46 then spring back to their original positions, which causes the spherical tips 50 to be located between the orthodontic arch wire 104 and the user's teeth 102. This, in turn, as shown in FIGS. 11 and 13, allows the subguard 14 to engage the user's braces 100, thereby creating a snug yet comfortable fit, while also still allowing the subguard 14 to be disengaged from the user's braces 100 by the user.

When the user desires to remove the subguard 14, and the mouthguard 10, from the user's mouth, the user pulls the mouthguard 10 and subguard 14 away from the user's teeth 102. The shape of the spherical tip 50 and the flexibility of the extension arm 48 again allows the spherical tip 50 to deflect around the orthodontic arch wire 104, which disengages the spherical tip 50 and the extensions 46 from the orthodontic arch wire 104 of the user's braces 100. Once the spherical tip 50 clears the orthodontic arch wire 104 it springs back to its original position, thereby disengaging the subguard 14 from the user's braces 100, and the mouthguard 10 may be removed from the user's mouth.

As seen in FIG. 14, each pair of extensions 46 of the subguard 14 are located on the distal side 44 of the subguard 14 such that there is only a small amount of clearance between the spherical tips 50 of the adjacent extensions 46 of the pair. That is, there is only a small gap between the two adjacent spherical tips 50 of the pair of extensions 46. Alternatively, due to the flexibility of the extension arms 48, the extensions 46 may be located such that the spherical tips 50 of a pair of extensions 46 actually come into contact with each other, such that the surfaces of the spherical tips 50 are resting against each other. Due to the flexibility of the extension arms 48, the spherical tips 50 may still deflect an amount sufficient to allow them to engage the orthodontic arch wire 104, as discussed herein, even when the spherical tips 50 rest against each other when they in a resting position.

While the tips of the extensions 46 of the preferred embodiment of the present invention are spherical in shape, the tips may alternatively have a cylindrical or circular shape, while retaining the characteristics of the spherical tips 50 described herein.

An alternative design for the extensions 46 is shown in FIG. 17. In this alternative design, the spherical tip 50 is omitted and the extensions 46 consist only of longer flexible extension arms 48. In this alternative design, the extension arms 48 take the form of rectangular or cylindrical projections that extend in pairs from the upper edge 52 and lower edge 54 of the distal side 44 of the subguard 14, with one of the extension arms 48 extending from the upper edge 52 of the distal side 44 of the subguard 14 and its matching pair extending from the lower edge 54 of the distal side 44 of the subguard 14.

Each pair of extensions 46 of the subguard 14 of this alternative design are sized lengthwise such that there is only a small amount of clearance between ends extension arms 48 of the pair. That is, there is only a small gap or slit between the two ends of the pair of extensions 46.

Where this alternative design for the extensions 46 is used and the orthodontic appliances of the user are braces 100, the pairs of extensions 46 allow the subguard 14 to be attached to the orthodontic arch wire 104 of the user's braces 100. As the subguard 14, and the mouthguard 10, is pressed against the user's braces 100 and teeth 102, the gap or slit between the pair of extension arms 48, and the flexibility of the extension arms 48, allows the orthodontic arch wire 104 of the braces 100 to slip through this gap or slit, after which the extension arms 48 are located between the orthodontic arch wire 104 and the user's teeth 102. This, in turn, allows the subguard 14 to engage the orthodontic arch wire 104 of the user's braces 100, thereby holding the subguard 14 and mouthguard 10 to the user's braces 100.

When the user desires to remove the subguard 14, and the mouthguard 10, from the user's mouth, the user pulls the mouthguard 10 and subguard 14 away from the user's teeth 102. The orthodontic arch wire 104 of the braces 100 again slips through the gap or slit between the pairs of extensions 46, thereby disengaging the extension arms 48 from the orthodontic arch wire 104 of the user's braces 100. Once the extension arms 48 clear the orthodontic arch wire 104 they return to their original position, thereby disengaging the subguard 14 from the user's braces 100, and the mouthguard 10 may be removed from the user's mouth.

While two designs for the extensions 46 of the subguard 14 are disclosed herein, the extensions 46 may take any form that allows the extensions 46, and therefore the subguard 14 and mouthguard 10, to engage the orthodontic appliances 100 of the user. For example, alternative shapes or configurations for the extensions 46 include hooks, J-shaped clasps, bars, and other similar shapes.

Additionally, while in the preferred embodiment pairs of extensions 46 are utilized, alternative designs may be configured to use single extension, rather than pairs, without departing from the present invention. Likewise, while the preferred embodiment utilizes single pairs of extensions 46 that are separated from other pairs of extensions 46, where a stronger engagement between the subguard 14 and the orthodontic appliances 100 of the user is desired, some or all of the pairs of extensions 46 may be located in close proximity to other pairs of extensions 46, provided that, in the case of braces 100, the location of the extensions 46 allows sufficient room for the brackets 106 of the braces 100.

While preferably the subguard 14 is flexible enough to adjust to the size, shape, and configuration of the user's teeth, mouth, and orthodontic appliances, the subguard 14 preferably cannot be formed and fitted in the manner in which, and at the temperatures at which, the outer guard 12 is fitted to the user. Thus, in the preferred embodiment, the mouthguard 10 is partially fitted, with the outer guard 12 being fitted and the subguard 14 not being otherwise fitted.

The subguard 14 of the mouthguard 10 may be constructed of any flexible medical grade plastic that is known in the art, such as medical-grade silicon, PVC material, or Kraton Isoprene Rubber. In the preferred embodiment, the subguard 14 of the mouthguard 10 is formed of a flexible medical grade polymer material that cannot be formed or softened at the low temperatures at which EVA may be softened and formed, but which may readily deflect to fit the mouth, teeth, and orthodontic appliances of the user. More preferably, the subguard 14 is formed of silicon rubber or medical PVC material. However, any other flexible synthetic or natural material may be suitable for forming the subguard 14.

In the preferred embodiment, the final mouthguard 10, once it has been fully assembled by the user, is a one-piece mouthguard. Therefore, in the preferred embodiment, the subguard 14 is secured to the outer guard 12, within the subguard channel 36 of the outer guard 12.

The subguard 14 may be secured to the outer guard 12 in any way known in the art, but is preferably mechanically secured to the outer guard 12 in such a way that the subguard 14 is engaged by the outer guard 12. Alternatively, the subguard 14 may be secured to the outer guard 12 with adhesives.

Most preferably, the subguard 14 is secured to the outer guard 12 in such a way that the subguard 14 is mechanically engaged by the outer guard 12, thereby directly securing the subguard 14 to the outer guard 12. In the preferred embodiment of the present invention, the subguard 14 is mechanically engaged by the outer guard 12.

Figure 15:
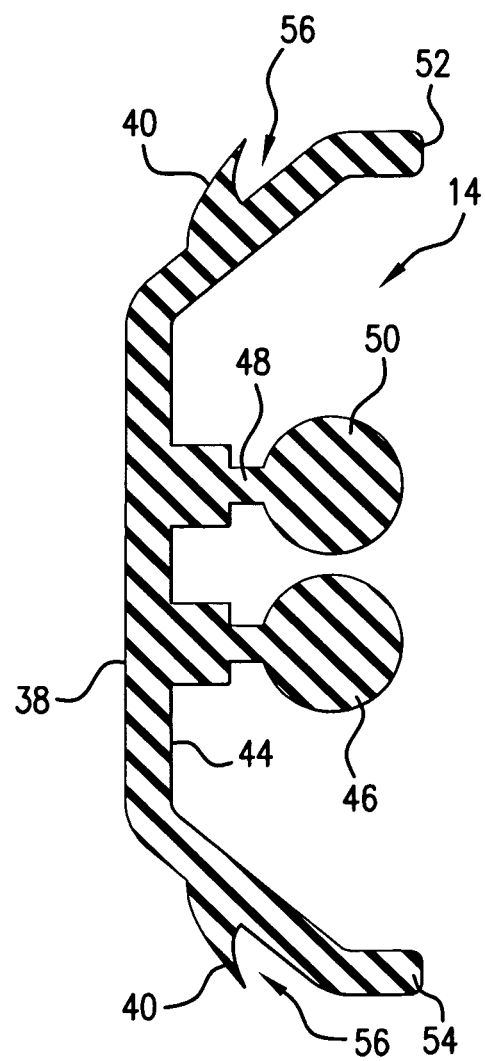
FIG. 15 is a cross-sectional view of a first alternative configuration of the subguard of the present invention.

In the preferred embodiment of the present invention, as seen in FIGS. 8 and 14, the subguard 14 includes a plurality of ridges 40 having a triangular-shaped cross section that project from the mesial side 38 of the subguard 14. In the preferred embodiment, there are four such ridges 40, with two ridges 40 on the upper mesial portion of the subguard 14 and two ridges 40 on the lower mesial portion of the subguard 14. However, alternatively, only two such ridges 40 may be used, as may be seen in FIG. 15, with one ridge 40 on the upper mesial portion of the subguard 14 and one ridge 40 on the lower mesial portion of the subguard 14.

The ridges 40 allow the subguard 14 to mechanically engage the outer guard 12. That is, when the outer guard 12 is fit to the mouth and teeth of the user as described herein, such as by the "boil and bite" method, the soft material of the outer guard 12 surrounds the ridges 40 and the ridges 40 project into and are embedded within the material of the outer guard 12. More specifically, the ridges 40 are embedded within the outer guard 12 when the softened material of the outer guard 12 flows into and fills the spaces or undercuts 56 adjacent to the ridges 40. Once the material of the outer guard 12 hardens in these spaces 56 adjacent to the ridges 40, the subguard 14 is mechanically secured to the outer guard 12 and the subguard 14 cannot be separated from the outer guard 12. That is, the embedding of the ridges 40 in the material of the outer guard 12 secures the ridges 40 within the outer guard 12 and, therefore, secures the subguard 14 to the outer guard 12 by mechanical engagement.

While the ridges 40 of the preferred embodiment are the structures discussed herein as being used to secure the subguard 14 to the outer guard 12 via mechanical engagement, it will be understood by those skilled in the art that various structures may be used in the place of the ridges 40 to allow the mechanical engagement between the subguard 14 and the outer guard 12. As such, it will be understood by those skilled in the art that various structures may be substituted for the ridges 40 without departing from the scope of the present invention, provided that such structures allow for mechanical engagement between the subguard 14 and the outer guard 12.

The mechanical engagement of the subguard 12 and the outer guard 14, as described herein, increases the strength of the connection between the subguard 14 and the outer guard 12. Optionally, an adhesive or adhesive strip 42 may be used to provide additional engagement between the subguard 14 and the outer guard 12, where the user desires such additional engagement, in which case the subguard 14 will have a design similar to that shown in FIG. 16. However, where the subguard 14 is mechanically engaged by the outer guard 12 as discussed herein, such mechanical engagement provides a sufficient connection between the subguard 14 and the outer guard 12 and an adhesive or adhesive strip 42 is not necessary and is merely optional. In the preferred embodiment, the subguard 14 is secured to the outer guard 12 solely by mechanical engagement.

If such an optional adhesive or adhesive strip 42 is used, the adhesive or adhesive strip 42 can aid the mechanical engagement of the subguard 14 and the outer guard 12 in preventing the separation of the subguard 14 from the outer guard 12. However, the mechanical engagement of the subguard 14 and the outer guard 12, as described herein, preferably allows the adhesive or adhesive strip 42 to be omitted, such that the subguard 14 is secured to the outer guard 12 solely through the mechanical engagement of the subguard 14 and the outer guard 12. The ability to omit the adhesive or adhesive strip 42 from the subguard 14 of the mouthguard 10 may reduce the cost of the mouthguard 10 and may also increase the user-friendliness of the mouthguard 10.

Alternatively, an adhesive or adhesive strip 42 may be used to secure the subguard 14 to the outer guard 12, either alone or in conjunction with the mechanical engagement of the subguard 14 and outer guard 12 as described herein. Where such an adhesive or adhesive strip 42 is used to secure the subguard 14 to the outer guard 12, the subguard 14 is first secured to the user's orthodontic appliances, such as braces 100, and then the outer guard 12 is fitted to the user's mouth and teeth, most preferably using the "boil and bite" process known in the prior art as discussed herein. The "boil and bite" process involves boiling the outer guard 12 in water for a time sufficient to sufficiently soften the outer guard 12. The outer guard 12 is then placed in the user's mouth, after the subguard 14 has been secured to the user's orthodontic appliances 100, and the user firmly bites down on the outer guard 12. Since the outer guard 12 has been softened by boiling the outer guard 12 in water, the outer guard 12, in response to the pressure from the user's mouth, teeth, and jaws, will conform to the shape and configuration of the user's mouth and teeth. Once the outer guard 12 begins to cool and becomes less soft and pliable, the outer guard 12 is then removed from the user's mouth and is allowed to fully cool, which causes the outer guard 12 to harden and set. Once the outer guard 12 has fully cooled, it retains its shape and is therefore fitted to the user's mouth and teeth.

Once the outer guard 12 has been fitted to the user's mouth and teeth, the subguard 14 may then be secured to the outer guard 12. Where the subguard includes an adhesive strip 42, the protective covering on the adhesive strip 42 is removed by the user and then the subguard 14 is secured to the outer guard 12 in the proper location within the subguard channel 36 by pressing the adhesive strip 42 of the subguard 14 against the outer guard 12 until the adhesive of the adhesive strip 42 secures the subguard 14 to the outer guard 12.

Where the adhesive or adhesive strip 42 is used in conjunction with the mechanical engagement between the subguard 14 and the outer guard 12, rather than in place of it, the adhesive may be applied to the subguard 14 or the protective covering on the adhesive strip 14 may be removed by the user prior to the user fitting the outer guard 12. As such, the subguard 14 is adhered to the outer guard 12 while the outer guard 12 is being fitted to the user's mouth.

Alternatively, where the subguard 14 does not include an adhesive strip 42, but the user still desires to use an adhesive to secure the subguard 14 to the outer guard 12, the user may use a dental adhesive to secure the subguard 14 to the outer guard 12. Any dental adhesive known in the art may be used as the adhesive of the adhesive strip 42 or the separate adhesive used to secure the subguard 14 to the outer guard 12. For example, a dental adhesive such as Polygrip® or Fixodent®, or other similar such adhesive, may be used.

Alternatively, it is possible to use the mouthguard 10 of the present invention without the subguard 14 being secured to or engaged by the outer guard 12. That is, the mouthguard 10 of the present invention may, at the user's option, be used as a two-piece mouthguard, with the two pieces being the outer guard 12 and the subguard 14. If the mouthguard 10 is used as a two-piece mouthguard, the subguard 14 is first placed within the user's mouth and secured to the user's orthodontic appliances 100 and then the outer guard 12 is placed within the user's mouth and covers the subguard 14 and the user's teeth and orthodontic appliances 100.

However, the use of the mouthguard 10 as a two-piece mouthguard is less preferable since the mouthguard 10 will not be retained within the mouth of the user as well as the preferred embodiment. That is, while the use of the subguard 14 would still allow the outer guard 12 to be used and to be fitted to the mouth and teeth of the user without becoming entangled in the user's orthodontic appliances 100, the outer guard 12 of the mouthguard 10 would likely be able to shift positions within the user's mouth and would not be held in place securely within the user's mouth as it is with the preferred embodiment, thereby reducing the overall comfort of the mouthguard 10. Such an alternative mouthguard 10, being a two-piece design, would also have reduced user-friendliness and ease-of-use compared to the preferred embodiment.

In order to use the mouthguard 10 of the present invention, after the user has fitted the outer guard 12 and secured the subguard 14 to the outer guard 12 as discussed herein, the user first places the mouthguard 10 in the user's mouth, over the teeth of the user's top jaw. The user presses the mouthguard 10 upward and backward, such that the mouthguard 10 slides over the teeth of the user's top jaw and the extensions 46 of the subguard 14 come into contact with the user's orthodontic appliances 100. The user then presses the mouthguard 10 toward the user's teeth 102, such that the extensions 46 of the subguard 14 engage the user's orthodontic appliances 100, as set forth herein. Once the extensions 46 of the subguard 14 engage the user's orthodontic appliances 100, the mouthguard 10 will be secured to the teeth and orthodontic appliances 100 of the user and retained within the user's mouth. The user then may participate in any desired sporting activity, while the mouthguard 10 of the present invention protects the user's teeth and mouth from injury and the user's orthodontic appliances 100 from damage and/or breakage and exhibits improved retention within the user's mouth compared to current prior art mouthguards. As such, the mouthguard 10 of the present invention allows the user to breathe and speak uninhibited during the sporting activity, thereby increasing the comfort of the mouthguard 10 and the user's performance during the sporting activity.

Preferably, as described herein, the outer guard 12 of the mouthguard 10 of the present invention may be user mouldable to suit the physical characteristics of the user, thereby making the mouthguard 10 partially mouldable. However, the outer guard 12 may alternatively be pre-moulded and thus be of the more basic type of mouthguard previously mentioned. In yet another alternative, the outer guard 12 of the mouthguard 10 of the present invention may be custom moulded using a cast or impression taken of the user's physical characteristics by a dentist or orthodontist.

In the preferred embodiment of the present invention, the outer guard 12 of the mouthguard 10 is custom fitted to a user's teeth 102 in a manner disclosed in the prior art, such as the "boil and bite" method described herein, while the subguard 14 is not. Therefore, a user with braces may mould the mouthguard 10 of the present invention to the characteristics of their own mouth and teeth without disturbing orthodontic braces, as the subguard forms a barrier between the custom-fit outer guard 12 and the braces 100, thereby preventing the softer thermoplastic of the outer guard 12 from becoming entangled with the components of the braces 100.

The use of the subguard 14 as part of the present invention permits the mouthguard 10 to be custom fit to a user's mouth and teeth without disturbing the user's braces 100. In addition, the moulding of the outer guard 12 of the mouthguard 10 to the specific characteristics of the user's mouth and teeth increases comfort and impact absorption of the mouthguard 10, thus reducing mouth and tooth injuries, as well as concussions.

The ease of insertion and removal of the mouthguard 10 of the present invention allows the mouthguard 10 to be used repeatedly without damage to the mouthguard 10 or the orthodontic appliances 100 of the user. Specifically, the subguard 14 is instrumental in the protection of the user's orthodontic appliances, such as the orthodontic arch wire 104 and brackets 106 of braces 100. The subguard 14 prevents the outer guard 12 from coming into contact with the braces 100 and embedding into undercuts or surrounding the orthodontic arch wire, causing difficulties with removing the mouthguard 10 and potentially causing damage to the braces 100 when the mouthguard 10 is removed. Enclosing or covering the user's braces 100 with the subguard 14 of the mouthguard 10 of the present invention allows for ease of removal of the mouthguard without causing or risking breakage of the components of the user's braces 100.

An additional benefit of the subguard 14 of the mouthguard 10 is improved retention of the mouthguard 10 within the user's oral cavity. Since the extensions 46 of the subguard 14 engage the user's orthodontic appliances 100, the mouthguard 10 is more easily retained in the proper position in the user's mouth and will not shift within the user's mouth when the user's jaws move, for example, when the user speaks or breathes. This improved retention of the mouthguard 10 allows the user to breathe and speak uninhibited during the sporting activity, thereby increasing the comfort of the mouthguard 10. Therefore, users are more likely to use and continue to use the mouthguard 10 of the present invention during sporting activities, which reduces the likelihood of injury to the user or the breakage of the orthodontic appliances caused by impacts suffered by the user during the user's participation in the sporting activity.

The mouthguard 10 of the present invention may be mass produced in several general sizes in order to allow the outer guard 12 and subguard 14 to already be close to the proper size for the user's mouth and teeth prior to the fitting of the outer guard 12. Additionally, by having several initial sizes for the mouthguard 10 to choose from, the amount of material necessary to produce the mouthguard 10 may be minimized.

The mouthguard 10 of the present invention may be used in all sports, but specifically for football, basketball, baseball, and other similar athletic activities.

It will be recognized by one skilled in the art that the size, configuration, or dimensions of the mouthguard 10 of the present invention may be adjusted to accommodate a variety of different individuals having different jaw sizes or jaw or tooth configurations, or to accommodate individuals with different types of orthodontic appliances.

While the invention has been described in the specification and illustrated in the drawings with reference to certain preferred embodiments, it will be understood by those skilled in the art that various changes may be made and equivalents may be substituted for elements thereof without departing from the scope of the present invention as defined in the appended claims. In addition, many modifications may be made to adapt a particular situation or material to the teachings of the invention, as defined in the appended claims, without departing from the essential scope thereof. Therefore, it is intended that the present invention not be limited to the particular embodiments illustrated by the drawings and described in the specification as the best modes presently contemplated for carrying out the present invention, but that the present invention will include any embodiments falling within the description of the appended claims.

What is claimed is:

1. A mouthguard comprising:
   an outer guard; and
   a subguard;
   wherein the subguard removably engages orthodontic appliances of an individual, wherein the subguard prevents the outer guard from becoming entangled with the orthodontic appliances, wherein the subguard is mechanically secured to the outer guard, and wherein the subguard includes a at least one ridge, wherein the ridge is embedded within the material from which the outer guard is constructed, and wherein the embedding of the ridge within the material from which the outer guard is constructed mechanically secures the subguard to the outer guard.

2. The mouthguard of claim 1 wherein the at least one ridge has a triangular cross section and wherein the at least one ridge is a plurality of ridges.

3. The mouthguard of claim 1 wherein the outer guard is custom fitted to the characteristics of the individual's mouth and teeth.

4. The mouthguard of claim 3 wherein the outer guard is made of an ethylene vinyl acetate copolymer.

5. The mouthguard of claim 1 wherein the subguard is made of a medical-grade plastic.

6. The mouthguard of claim 1 wherein the subguard includes at least one extension that extends from a distal surface of the subguard and wherein the at least one extension removably engages the orthodontic appliances of the individual.

7. The mouthguard of claim 6 wherein the at least one extension comprises an extension arm that extends from the distal surface of the subguard.

8. The mouthguard of claim 6 wherein the at least one extension comprises an extension arm that extends from the distal surface of the subguard and a tip that is connected to the extension arm opposite the distal surface of the subguard.

9. The mouthguard of claim 8 wherein the tip of the extension has a substantially spherical shape.

10. The mouthguard of claim 9 wherein extension arm of the at least one extension is flexible and allows the extension to have a deflected configuration wherein the mouthguard may be removed from the mouth of the individual and a resting configuration wherein the extension removably engages the individual's orthodontic appliances.

11. The mouthguard of claim 6 wherein the at least one extension comprises a plurality of extensions.

12. The mouthguard of claim 11 wherein the plurality of extensions extend in pairs from the distal surface of the subguard.

13. The mouthguard of claim 12 wherein the plurality of extensions are laterally spaced from each other and the lateral spacing of the extensions correspond with the lateral spacing of the orthodontic appliances of the individual.

* * * * *